United States Patent [19]

Rothenberg

[11] Patent Number: 4,909,261
[45] Date of Patent: Mar. 20, 1990

[54] TRACKING MULTIELECTRODE ELECTROGLOTTOGRAPH

[75] Inventor: Martin Rothenberg, Dewitt, N.Y.

[73] Assignee: Syracuse University, Syracuse, N.Y.

[21] Appl. No.: 310,592

[22] Filed: Feb. 13, 1989

[51] Int. Cl.$^4$ ............................................. A61B 5/10
[52] U.S. Cl. .................................... 128/734; 128/774
[58] Field of Search ............... 128/734, 774, 777, 782, 128/739; 381/41, 48–49

[56] References Cited

U.S. PATENT DOCUMENTS

| | | |
|---|---|---|
| 3,026,449 | 3/1962 | Rappaport . |
| 3,340,867 | 9/1967 | Kubicek et al. ................. 128/734 X |
| 3,871,359 | 3/1975 | Pacela ................................ 128/734 |
| 4,139,732 | 2/1979 | Fourcin . |
| 4,287,895 | 9/1981 | Hori .................................... 128/777 |
| 4,310,002 | 1/1982 | Takinishi et al. ............... 128/777 X |

FOREIGN PATENT DOCUMENTS 0641960  1/1979  U.S.S.R. ............................... 128/734

OTHER PUBLICATIONS

Rothenberg, Some Relations Between Glottal Air Flow and Vocal Fold Contact Area, 90 ASHA Reports, No. 11, 88–96, Dec. 1981.
Baker, Clinical Measurement of Speech and Voice, pp. 216–240, 1981.
Rothenberg and Mahshie, Monitoring Vocal Fold Abduction Through Vocal Fold Contact Area, 31 J. of Speech & Hearing Res., 338–351, Sep. 1988.
Harrington, Intro. to Electromagnetic Engineering, 68–69, 1958.
Childers and Krishnamurthy, A Critical Review of Electroglottography, 12 CRC Critical Reviews in Biom. Engineering, 131–161, 1985.

Primary Examiner—Angela D. Sykes
Attorney, Agent, or Firm—Wall and Roehrig

[57] ABSTRACT

A tracking multielectrode electroglottograph has a number of electrodes that are located about each other in opposed arrays placed on either side of a subject's neck during vocalized speech or singing. Each pair of opposed electrodes within the arrays is coupled to a separate channel of the electroglottograph electronics, which, in turn, provides an output signal which reflects, in large measure, the variation with time of the area of contact between the vibrating vocal folds within the subject's larynx. Each channel has a send circuit containing a signal generator that is isolated from the other channels and which produces a high frequency carrier that is synchronized with the carriers from the other channels so as not to produce beats. Each channel also has a receive circuit with input connected to the output of the respective send circuit and to the respective pair of opposed electrodes. The electrodes and the send and receive circuits can be connected either in parallel or in series with each other. The receive input is connected to an amplitude modulation demodulator, which can be a rectifying envelope detector. The relative amplitudes of the output signals from the associated channels indicate the position of the subject's larynx with respect to the several pairs of electrodes and which signal or signals best represent the variation of vocal fold contact area. Some differences in the spatial patterning of the contact area can also be seen in the differences between the waveforms from the various channels. An additional feature provides an indication of when the output of the electroglottograph is not sufficient for a reliable indication.

21 Claims, 8 Drawing Sheets

FIG. 3A — RAISED 10 MM
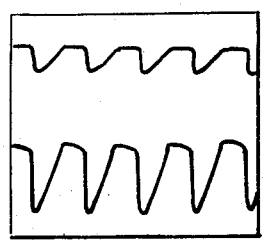
FIG. 3B — RAISED 5 MM
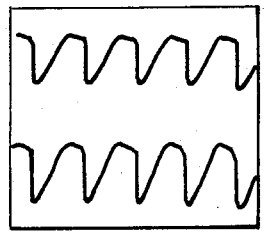
FIG. 3C — ELECTRODES PLACED FOR APPROXIMATELY EQUAL AMPLITUDES
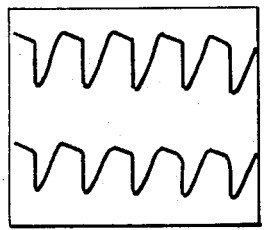
FIG. 3D — LOWERED 5 MM
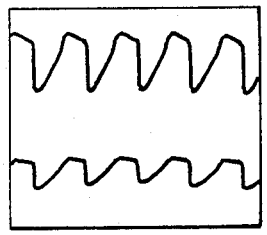
FIG. 3E — LOWERED 10 MM
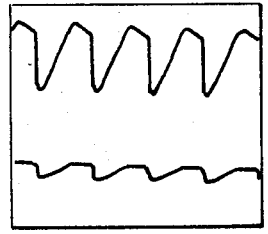

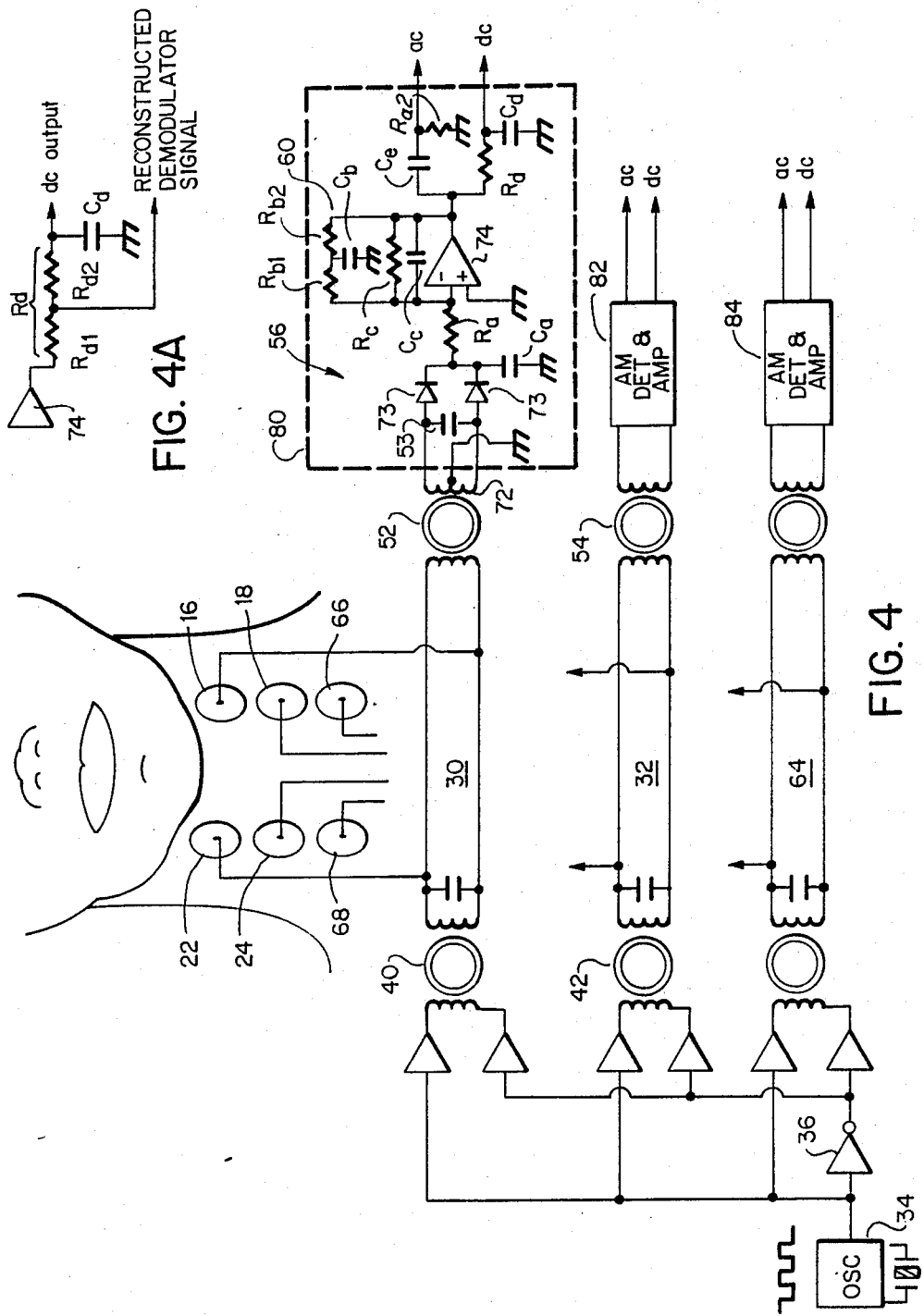

TRACKING MULTIELECTRODE ELECTROGLOTTOGRAPH

BACKGROUND OF THE INVENTION

This invention relates to the measurement of physiological parameters associated with human speech, and is more particularly directed to electroglottograph apparatus, sometimes referred to as a laryngograph.

Because of the relative inaccessibility of the larynx or voice box, and the rapidity of the movements involved, it has been difficult to realize direct imaging of the movements of vibrating vocal folds of the human larynx. The imaging of the vocal fold movements during speech or singing generally requires techniques that are inconvenient and/or uncomfortable. For example, these direct imaging techniques can employ a mirror located in the oropharynx or a transnasal fiberoptic catheter. Other techniques, such as high-speed x-ray or stroboscopic photography, can present an unacceptable risk to the subject.

For the above reasons, a preferred technique for observing oscillatory movements of the vocal folds within the human larynx has been to use a small electric current through the neck at the level of the larynx to record the small changes in electrical impedance within the neck that are caused by the vocal fold movements. Preferably, an alternating current is applied for this, at a frequency of at least about one megahertz and a current of no more than about ten milliamperes.

An electroglottograph (EGG) is an electronic device for non-invasive measurement of the time variation of the transverse electrical impedance of the neck at the level of the larynx during voiced speech or singing, in order to obtain a waveform related to the vibratory patterns of the vocal folds within the larynx. In current practice, the electrode size and location, the nature of the electrical current, and other system parameters are chosen so as to make the voice-synchronous ac component of an electroglottograph output a waveform whose amplitude is related as closely as possible to the variation of vocal fold contact area (VFCA). It is this voice-synchronous ac component that is normally referred to as the EGG waveform. The variation in electrical impedance measured by the EGG waveform, and which is caused by the vocal fold contact area, is rarely much more than one or two percent of the total neck impedance, and in some subjects the variation can have a peak-to-peak value of less than 0.1% of the total neck impedance.

There are several commercially available electroglottograph devices, one of which is described in U.S. Pat. No. 4,139,732. That patent is addressed to the problem of efficiently demodulating an amplitude modulated carrier in which the modulation is only a small percentage of the carrier and proposes a technique in which only that part of the carrier waveform above a preset threshold level is demodulated, with feedback to the carrier source used to keep the amplitude of the carrier just above the threshold. The patent also addresses the problem of eliminating the electrical currents on the surface of the neck from the carrier to be demodulated, by means of a guard ring about each electrode.

The voice-synchronous component of the translaryngeal electrical impedance tends to repeat at the vibratory frequency of the vocal folds —a frequency which is generally above about 100 Hz and is rarely below about 50 Hz. However, an electroglottograph can also provide a lower frequency waveform that reflects to some degree the slower, non-vibratory motions within the larynx and movements of the entire larynx within the neck. Movements of this nature that are of greatest interest in the measurement of speech and singing include the gross abductory (pulling apart) or adductory (pressing together) movements of the vocal folds during phonation and vertical movements of the entire larynx structure. Such abductory/adductory movements and vertical movements occur continuously during natural speech or singing, both to satisfy the demands of vowel and consonant articulation and to enable the various parts of the larynx to adjust for the desired pitch and voice quality. A noninvasive system for measuring these parameters would be useful in various types of speech training, as, for example, foreign language instruction and speech training for the deaf. J. J. Mahshie, et al., *Speech Training Aids for Hearing Impaired Individuals: III. Preliminary Observations in the Clinic and in Children's Homes*, Journal of Rehabilitation Research and Development, Vol. 25, No. 4, pp. 69–82 (1988). Since vertical movements of the larynx are important in the mechanism of pitch control, they are also of great interest in singing pedagogy. All such non-vibratory movements are generally restricted to frequencies below about 20 Hz, since they are limited by the response times of the underlying skeletal musculature. Unfortunately, since the low frequency components of the translaryngeal impedance reflect many such effect simultaneously, there has been little success in measuring vocal fold abduction/adduction or vertical movements of the larynx using the low frequency EGG components. M. Rothenberg and J. J. Mashie, *Monitoring Vocal Fold Abduction Through Vocal Fold Contact Area*, J. Speech Hear Res., Vol. 31, pp. 338–351 (1988). Even for the measurement of VFCA, current techniques of electroglottography, while being potentially convenient, inexpensive, and non-invasive, still have residual problems. To obtain waveforms that represent primarily VFCA, current EGG units require careful and accurate placement of the electrodes with respect to the vocal folds. However, the larynx is often difficult to locate by conventional techniques such as palpation, and this is especially true with women and children and with subjects that are somewhat obese. Even with subjects for which the location of the larynx is easily observed, the continuous vertical migration of the larynx during speech or singing reduces the reliability of the output waveform. Moreover, with a small proportion of subjects, even an optimal positioning of the electrodes may not produce a waveform accurately depicting VFCA. Whether the problem in these cases is improper electrode position or neck physiology, the presently available units do not indicate unambiguously those occasions in which the signal provided by them is not to be trusted.

Yet another reason that electroglottography is not relied on by practitioners is that the various waveform features of most interest to the clinician have not yet been clearly charted. However, this is believed to result principally from the problems mentioned above, as it would constitute a waste of effort to document in detail artifacts, noise, and characteristics of a device that cannot be trusted. Finally, a limitation of all current techniques is that they indicate only the variation of the total contact area and do not differentiate in any way between different patterns of contact across the length of the vocal folds. D. G. Childers and A. K. Krishnamurthy, *A Critical Review of Electroglottography*, CRC Critical Reviews in Bioengineering, Vol.12, No. 2, pp. 131–161 (1985). Such differences in the contact pattern in the horizontal or anterior-posterior dimension are believed to be an important factor in determining vocal efficiency, and a convenient, noninvasive method for their measurement would be of significant value.

OBJECTS AND SUMMARY OF THE INVENTION

It is an object of this invention to provide an electroglottograph that avoids the drawbacks of the prior art.

It is a more specific object of this invention to provide an electroglottograph that permits easy and accurate location of its electrodes at the appropriate position for obtaining a clear, low-noise output signal.

It is a still further object of this invention to provide an electroglottograph that permits tracking of vertical movements of the larynx during speech or singing.

It is a still further object of this invention to provide an electroglottograph that differentiates between different spatial patterns of contact between the vocal folds during vocalization.

In accordance with one aspect of this invention, the electroglottograph has at least first and second channels, with each channel having an RF signal source with output leads, which is composed of an oscillator and an RF amplifier or the like, the output of which is isolated from the output of the corresponding means of the other channel and which produces a high-frequency carrier that is synchronized to the carrier generated in the other channel so as not to produce interchannel interference such as beats. Each channel also has receive circuitry with input leads. In each channel there are also respective left and right electrodes to be disposed in contact with the skin on the left and on the right side of the subject's neck at the location of the larynx. The left and right electrodes of each channel are connected to the output leads of the send circuitry of that channel and to the input leads of the receive circuitry. For each channel, the send output leads, the electrodes and the receive input leads are preferably connected in a parallel configuration, but can be connected in series. When the send output leads, the receive input leads and the electrodes are connected in a parallel configuration, the electrical impedances presented by the send and receive circuits should preferably b greater than the electrical impedance of the neck between the electrodes. With a series connection, these impedances should preferably be smaller than that of the neck.

The receive input leads in each channel are connected to an envelope detector or other AM demodulating means which provides an output signal having an ac component and a dc or low frequency component. The ac component, which is the waveform normally referred to as the EGG output signal, includes frequency components at and above the frequency at which the vocal fold vibratory pattern tends to repeat (often referred to as the voice fundamental frequency), and measures the vibratory pattern of the vocal folds. The dc or low frequency portion of the demodulated signal measures the average impedance of the neck between the electrodes and variations thereof that are substantially slower than the vocal fold vibrations.

In coupling the electrodes to the send oscillator or amplifier and to the receive circuitry, respective send and receive transformers can be employed that perform the functions of impedance matching, tuning to the carrier frequency and isolation of the three elements being coupled at frequencies other than the RF carrier frequency. However, one or both of the transformers in each channel could be replaced by other standard RF coupling means, such as inductor-capacitor circuits, that perform similar functions. An optional RF amplifier can also be employed at the receiver input to increase the level of the signal presented to the demodulator.

The left and right electrodes of the first channel can be disposed on the subject's neck vertically above the respective left and right electrode of the second channel, so that variations in the relative amplitudes of the respective demodulated output signals can be used to track the vertical position of the glottis, and, thereby, the vertical position of the entire larynx, since the vertical position of the glottis within the larynx varies relatively little as the larynx moves vertically. The RF signal source means of the second (and third, etc.) channel can preferably include logic circuitry that provides alternating high and low levels, and an input terminal that is coupled to a driver oscillator common to the first channel, which is preferably crystal controlled. In a preferred embodiment the electrodes are disks of between 0.5 and 1.5 cm in area, and are spaced above one another by a distance of substantially five to ten millimeters. Alternatively, the electrodes of the first channel can be located posterior to the electrodes of the second channel, to form a horizontal array, so that the first channel measures to a greater extent the contact at the posterior half of the vocal folds and the second channel measures to a greater extent the contact along the anterior half of the vocal folds. With a greater number of channels, a two-dimensional array could be formed to provide both the vertical tracking and the horizontal contact pattern information. For brevity, the following discussion emphasizes a vertical array.

For a vertical array, guard channel electrodes can also be provided to increase efficiency by reducing the horizontal fringing fields of the electrodes of the active channels, R. Harrington, *Introduction to Electromagnetic Engineering*, McGraw Hall, pp. 68,69 (1958). The guard channel electrodes could include at least a pair of opposed elongated vertical guard electrodes that extend vertically alongside the superposed electrodes of the first and second (and third, etc.) channels.

To provide a better isolation of the electric fields produced by each channel, the various channels can be time-multiplexed by providing energy to only selected channels at any one instant and simultaneously sampling the outputs of those channels selected. Switching of the send signal is preferably accomplished by standard logic integrated circuits, while sampling of the outputs is preferably accomplished by standard sample-and-hold circuitry. The sampling rate for any one channel is preferably at least twice the frequency of the highest Fourier component of interest in the EGG waveform.

The EGG system of this invention with its multielectrode array provides simultaneous EGG measurements at a number of neck locations that are separated by a small amount in the vertical and/or horizontal dimension. The outputs from this array can be scanned to determine the optimal electrode position by assessing the relative amplitudes of the outputs from the various electrode pairs. This system can also track the position of the larynx as it moves vertically during speech or singing. Optimum performance can be attained because of the advantage of being able to determine the optimal position from the relative amplitudes of the output signals. The multi-channel design as described above provides separate, non-interfering fields for each electrode pair, and, consequently, more electrodes can be added without signal degradation. In addition, the electrical design does not rely on automatic level adjusting techniques. As a result, the output from each electrode pair can be calibrated in terms of percent modulation of the electrical current, that is, the percent ratio of the ac or EGG-signal potion of the demodulator output to the dc portion. Thus, the actual percent modulation and a range of percent modulation sufficient for proper operation can both be developed and displayed for the clinician.

The EGG output signals from each channel can be applied to an oscilloscope to produce representative oscilloscope traces, or can be applied to any other suitable multi-channel display device. A logic circuit could also be incorporated for automatically selecting the strongest of the several channel output signals as the EGG output. When used in this way, the placement of the array on the neck would not be as critical as with present EGG units. Alternatively, the EGG output could be taken from fixed, predetermined channels in the array, and electronic circuitry used to compare the output amplitudes of the various channels to provide the user with a meter or bar graph indication of the correct array position.

When used as a tracking electroglottograph to track vertical movements of the larynx with respect to the array, the position of the array on the neck would be kept invariant, and a tracking signal computed that is proportional to the vertical position of the electrode pair generating the strongest output. In this tracking function, interpolation equations based on the relative amplitudes of the ac signals from neighboring channels can be used to provide a spatial resolution finer than the spacing of the electrodes. In this way, movements of the larynx at least as small as 2 or 3 millimeters can be resolved.

Circuitry can also be readily added to the electroglottograph unit described herein, in any of its embodiments, for automatically extracting interpretive data of the types commonly obtained from present units, including the period of the glottal vibratory cycle, short term variations in this period (sometimes referred to as jitter), and the open or closed quotient (duty cycle) of the vibratory motion during each period.

The above, and many other objects, features and advantages of this invention will be more fully understood from the ensuing description of a preferred embodiment, which should be considered in connection with the accompanying Drawing.

BRIEF DESCRIPTION OF THE DRAWING

FIG. 2A is a detail view of a portion of the embodiment of FIG. 2.

FIGS. 3A–3E are oscilloscope traces of electroglottograph outputs showing the relative signal strength of two channels in a vertical array as a function of the location of the EGG array on the subject's neck. In each trace, an upward movement of the trace represents less vocal fold contact.

FIG. 4 is a schematic electrical diagram of a multichannel EGG device according to another embodiment of this invention.

FIG. 4A is a detail view of a portion of the embodiment of FIG. 4.

DETAILED DESCRIPTION OF THE PREFERRED EMBODIMENTS

Figure 1:
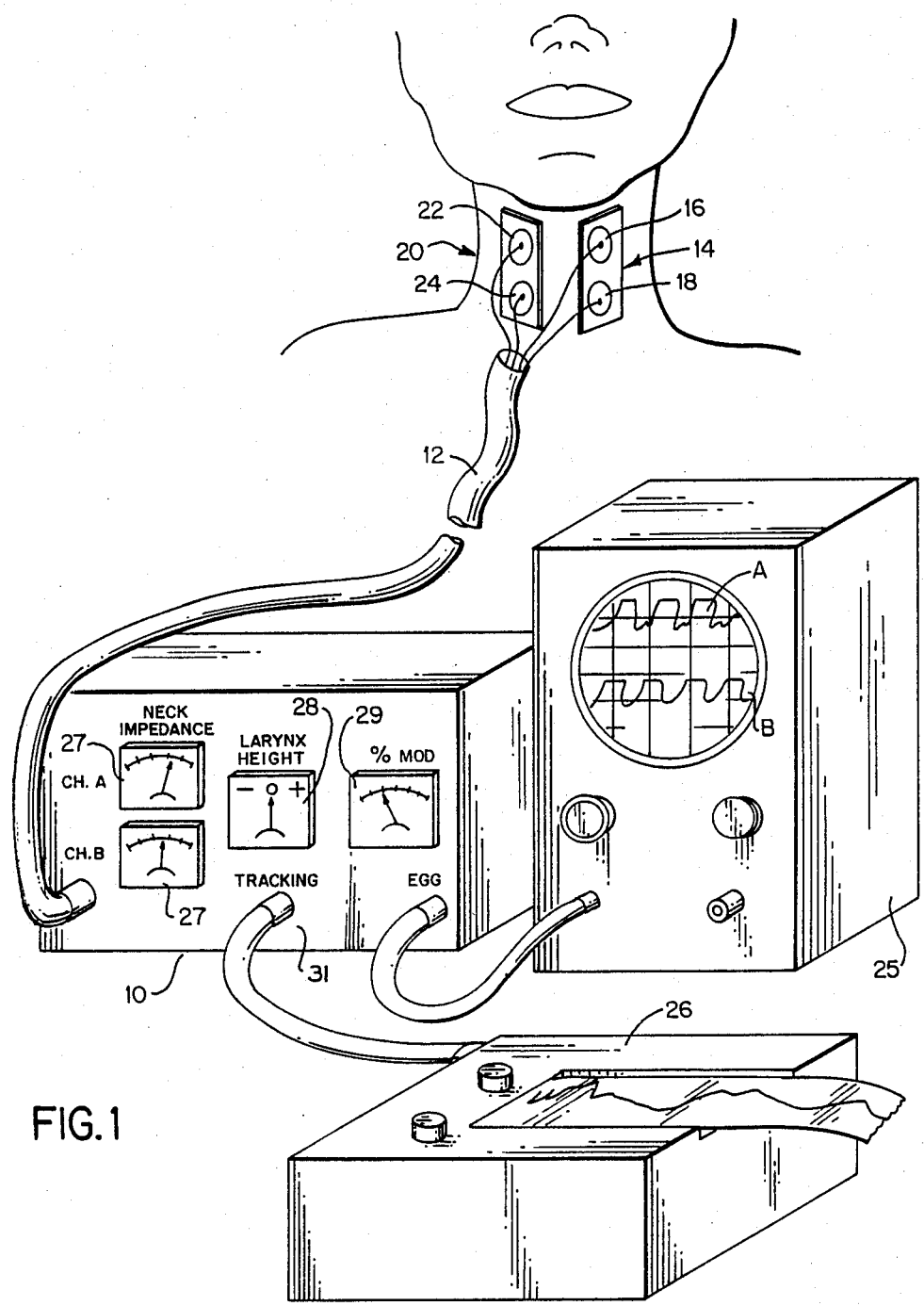
FIG. 1 is a schematic perspective view of an electroglottograph (EGG) according to one preferred embodiment of this invention.

With reference to FIG. 1 of the Drawing, a tracking multielectrode electroglottograph or TMEGG is shown as a small EGG electronics unit 10 having a cable 12 connecting to multicontactor or multielectrode arrays 14 and 20 for providing simultaneous EGG measurements at a plurality of neck locations, preferably separated along the vertical dimension with respect to the subject's neck. A left electrode assembly 14 consists of upper and lower superposed electrodes 16,18 and a right electrode assembly 20 consists of superposed upper and lower electrodes 22,24. The electrodes are here shown to be round in shape, but can have other shapes such as square or rectangular. The left electrode assembly 14 nd right electrode assembly 20 are situated on a subject's neck across from one another at approximately the location of the larynx or voice box. These are preferably carried on a collar, cuff or other support (not shown) which can be easily positioned on the subject's neck. The EGG unit 10 has an output connector coupled to a multi-channel oscilloscope 25, here showing upper and lower traces A and B. The upper trace corresponds to the signal generated between the upper pair of electrodes 16 and 22, while the lower trace corresponds to the signal generated between the lower pair of electrodes 18 and 24. The electrodes in the figure are shown as a vertical array, but also could be situated as a horizontal (anterior-posterior) array for use in locating the array optimally in the horizontal direction or for recording vibrational pattern differences along the length of the vocal folds.

Optional dc meters or bar-graph units 27 are connected to the dc or low frequency outputs of the EGG electronics 10 and can be calibrated to indicate the average electrical impedance of the neck between each electrode pair.

The ac outputs of the EGG electronics unit 10 can be scanned or compared to determine the optimal electrode position. In one method, proper positioning can be established by observing and comparing on the oscilloscope the relative amplitudes of the ac outputs A and B of the various channels representing the various electrode pairs in the arrays 14,20. Alternatively, the amplitudes of the ac outputs can be compared by electronic circuits within the EGG unit and the result presented as meter or bar-graph indication 28. In a preferred method with a two-channel array, a zero center scale indication would indicate that the ac outputs were equal in amplitude and, therefore, that the glottis was approximately centered vertically between the electrode pairs. A non-zero indication would indicate a non-centered position of the electrodes, and the polarity of the indication would indicate the direction that the electrodes should be moved to obtain a centered position. Since the voltage driving the indicator 28 can also be used to track the position of the glottis or larynx as it moves vertically during speech or singing, the unit can be employed as a tracking multielectrode electroglottograph or TMEGG. The voltage driving the indicator 28 can be output to a connector 31 for this purpose, to be recorded or to drive a chart recorder 26 or other similar display instrument.

An optional meter or bar graph unit 29 can also display the percent modulation of the RF carrier in each channel caused by the vocal fold movements, or, preferably, only the percentage modulation of the channel in which it is strongest, in order to allow the operator to determine whether the modulation is adequate for providing a reliable waveform. The indication would preferably be derived from the amplitude of the ac output for the channel selected and the magnitude of the dc output.

In the two-channel vertical array embodiment described herein, the noise level remains at a minimum, so that good performance can be attained with electrode small enough to be employed in a multielectrode array. Highly reliable low-noise performance is attained without need for the automatic level adjustment technique of the prior art.

Figure 2:
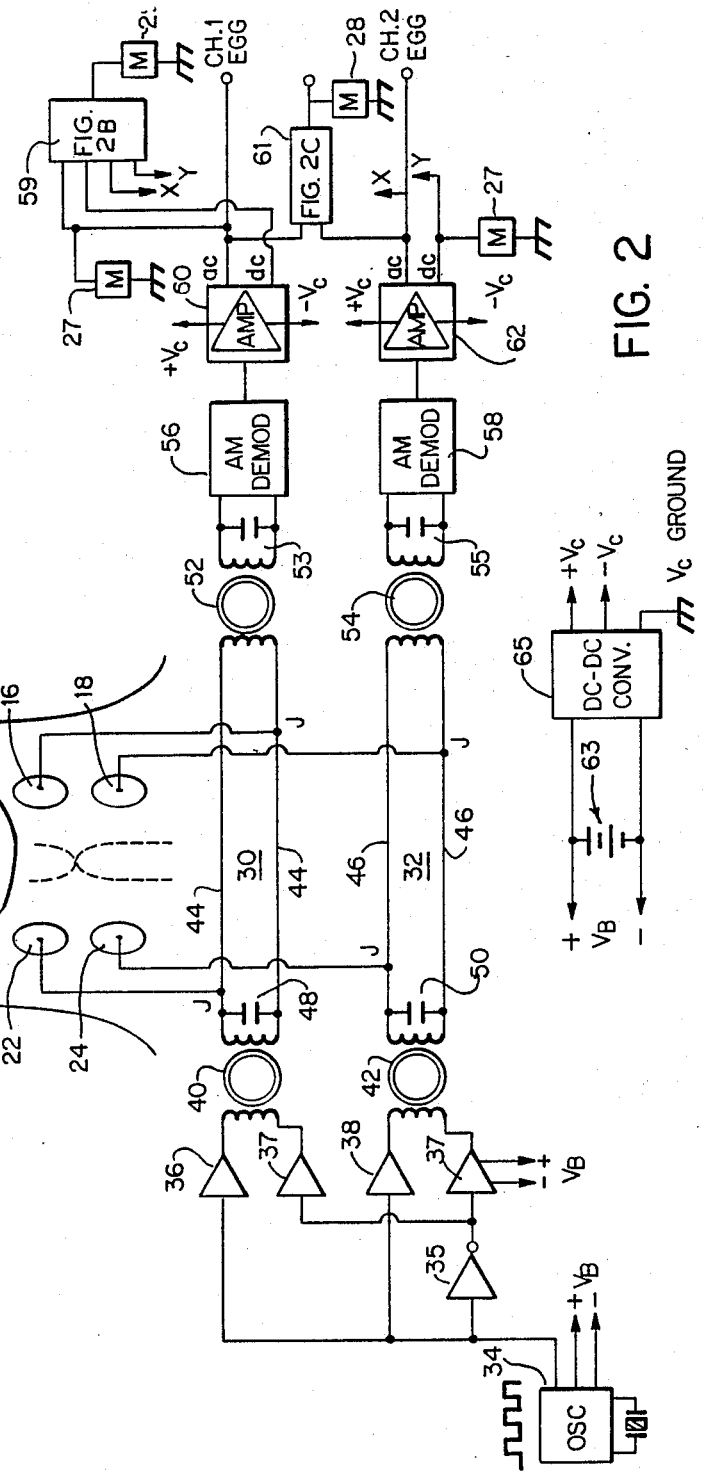
FIG. 2 is an electrical schematic diagram of the electroglottograph of the FIG. 1 embodiment.

The two-channel configuration of this embodiment is illustrated schematically in FIG. 2. In this embodiment a crystal-controlled oscillator having a logic level output 34 and an inverter logic circuit 35 provides a fixed frequency clocking signal and its inverse to each of two pairs of logic circuits 36,37 and 38,39. These logic circuits 36, 37, 38 and 39, which can be either noninverting buffer amplifier types or inverting types, serve as mutually isolated RF amplifiers, that is, carrier signal sources which provide the same RF carrier in phase, but independently, to respective send-side matching transformers 40 and 42, that have their primaries connected respectively to outputs of the logic circuits 36,37 and 38,39. There are capacitors 48 and 50 bridging the secondaries to tune the conjoined send transformer and lead assembly to the frequency of the RF oscillator. Pairs of conductors 44, 46 connect the secondaries of the send transformers 40 and 42 to the respective primaries of first and second receive-side matching transformers 52 and 54. Each of these latter transformers has its secondary connected respectively to a demodulator circuit, in this instance to AM envelope detectors 56 and 58, which are followed by respective amplifiers 60 and 62 that provide respective upper and lower ac and dc output signals. The detectors 56,58 could instead be coherent detectors. Capacitors 53 and 55 tune the receive transformer secondaries to the frequency of the RF oscillator.

For maximum efficiency of operation, the junction points between the send and receive transformers, each labeled J in FIG. 2, should be physically located lose to their respective electrodes. Thus, a more accurate representation of a junction J would e as shown in the detail in FIG. 2A.

The use of logic circuit or switching amplifiers removes the small random variations in amplitude that would be introduced by a linear amplifier. The conversion from a switched or square RF waveform to a more sinusoidal waveform is then effected by the tuned send transformer. This arrangement reduces amplitude modulation noise in the send waveform essentially to the noise present in the power supply voltage at the send amplifier.

In order to minimize or eliminate power supply noise, a battery power supply 63 is incorporated in the unit 10 to supply battery voltage $V_B$ to the various send circuit elements. A dc-to-dc converter 65 can preferably supply the required receiver power supply voltages $V_C+$ and $V_C-$ while providing a high degree of isolation at the carrier frequency between the receive circuitry and the send circuitry, the latter of which is powered directly by the battery voltage $V_B$.

The configuration in FIG. 2 is considered to be two-channel parallel, as the pair of upper electrodes 16,22 are connected to respective ones of the two conductors 44 of the upper or first channel 30, while the lower electrodes 18 and 24 are connected to respective conductors 46 of the second or lower channel 32. In other words, the impedance of the conduction path through the neck is in parallel with both of the transformer windings.

Figure 2B:
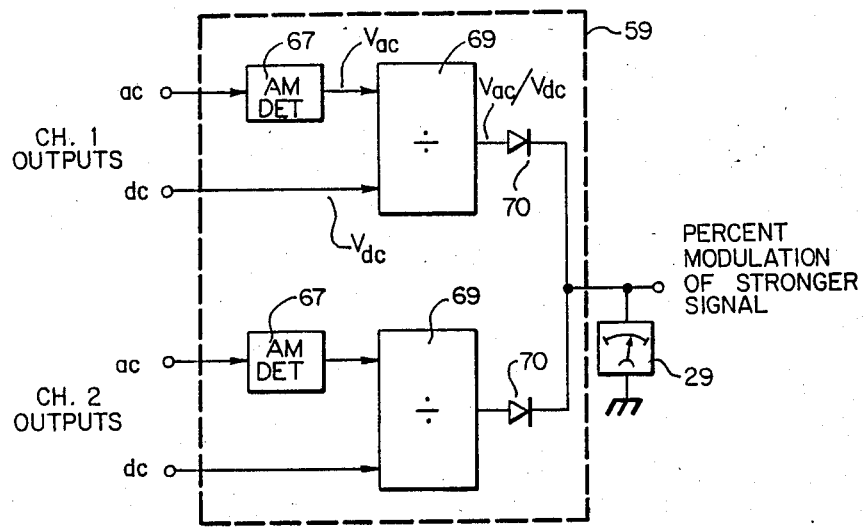
FIG. 2B is a schematic diagram of the computation circuitry 59 in the embodiment of FIG. 2 for determining the percent-modulation of the carrier in the channel having the greatest percent-modulation.

The simultaneous dc and ac outputs for each channel allow circuitry to be added to the embodiment of FIG. 2 to indicate to the user the percent modulation of the RE carrier for that channel having the greatest percent modulation. This would enable the user to judge the reliability of the EGG signal as an indicator of vocal fold contact area. A certain minimum value might be designated as acceptable in a particular application. A preferred embodiment for this circuitry is indicated in FIG. 2B. This includes amplitude measurement circuits 67 with inputs coupled to the respective ac channel outputs, which derive a standard measure of the ac wave amplitude, such as peak-to-peak or rms. The outputs $V_{ac}$ of the amplitude measurement circuits 67 in each channel and the respective dc channel outputs $V_{dc}$ are connected as inputs to respective ratio or divider circuits 69 which compute the percent modulation of the RF carrier in each channel as the ratio of $V_{ac}$ to $V_{dc}$.

The dividers 69 supply outputs representing the percent modulation in the respective channels to diodes 70 which have their cathodes connected together to an output and/or a meter 29 or other indicating device. At this output, only the higher of the various percent modulation outputs will be present, since only the diode having its anode connected to the highest voltage will conduct.

The divider outputs provide a direct representation of the percent modulation of the RF carrier that is caused by the vocal fold movements. However, the divider outputs will also be a good representation of percent modulation of the neck impedance that is caused by the vocal fold movements, providing the source impedance of the send circuitry and the input impedance of the receive circuitry are both much higher than the neck impedance (as has been stated to be preferable with a parallel electrode connection), since under these conditions the electrode current remains substantially constant and, therefore, the amplitude of the interelectrode voltage will vary in approximate proportion with the magnitude of the neck impedance. In this case, $V_{dc}$ will be much smaller than $V_{dco}$, where $V_{dco}$ is the value of the voltage $V_{dc}$ when the electrodes are off the neck and not in contact. If these conditions do not hold, a more accurate result can be obtained by any operation equivalent to multiplying $V_{dc}$ by the factor $(1-[V_{dc}/V_{dco}])$ before applying it to the divider input.

However, since the neck impedance (which determines $V_{dc}$) varies much less between individuals than does the differential change in impedance cause by vocal fold contact (which causes $V_{ac}$), the latter complication is not likely to be necessary in a practical EGG design, as long as the divider output is properly calibrated for the range of neck impedances to be found in practice. In fact, for many applications it may be possible to eliminate the use of the actual $V_{dc}$ in the percent modulation computation 59, and replace tee divider circuits 69 with a multiplicative constant, or gain factor, representing an average value of neck impedance for the population being tested.

Figure 2C:
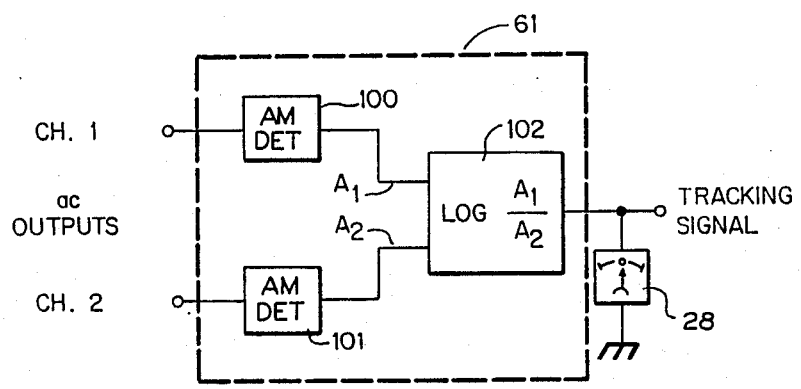
FIG. 2C is a schematic diagram of computation circuitry in the embodiment of FIG. 2 for developing an electrical signal that tracks the vertical position of the larynx with respect to the vertical center of a two-electrode-pair array.

The amplitudes, whether peak-to-peak, rms, or some other measure, of the various channel ac outputs of a vertical array can also be used to locate and track the position of the glottis with respect to the array. A preferred embodiment for a tracking system to be used with a two-channel array is shown in FIG. 2C. The circuits 100 and 101 measure the amplitudes of the ac components of each channel, and can, for economy, be the same circuits 67 used in the percent-modulation measurement system shown in FIG. 2B. The circuit of 102 receives the outputs $A_1$ and $A_2$ of circuits 100 and 101 and computes the logarithm of their ratio. The resulting signal will have a value of zero when the amplitudes are equal, a positive value that varies directly with position when the glottis is closer to the Channel 1 electrodes and a negative value that varies directly with position if the glottis is closer to the Channel 2 electrodes. This signal can be made available to the user at a tracing signal output connector and/or displayed by means of a zero-center meter or other such indicator 28. Either of the circuits in FIGS. 2B and 2C can be carried out with either analog circuit components or digital computations.

Typical output waveforms for the two-channel parallel vertical array embodiment are shown in FIGS. 3A through 3E for a typical, healthy non-obese adult male subject. In this embodiment, the RF frequency used was 2 MHz and the electrodes were silverized circular disks, 18 mm in diameter, and separated by an eight millimeter vertical gap. In this sequence, the electrodes were shifted vertically downward by increments of about 5 millimeters during similar repetitions of the vowel /a/, so that the resulting waveforms serve to show the resolving power of even this small array of two electrode pairs. FIGS. 3-3E respectively show the arrays 14 and 20 situated with the vertical center of each array about ten millimeters above the larynx, five millimeters above the larynx, approximately at the level of the larynx, five millimeters below the larynx, and ten millimeters below the larynx, respectively. The waveforms indicate that with this typical subject and with the electrodes used, larynx movements as small as 2-3 millimeters will be resolvable from changes in the relative amplitudes of the upper and lower TMEGG waveforms. Additional resolution can be obtained with yet smaller electrodes, although there may be an accompanying, but tolerable, increase in noise.

In the center pair of traces of FIG. 3C, the similar amplitudes in the upper and lower traces implies that the larynx was at a level approximately midway between the electrode pairs 16,22 and 18,24. Moreover, the similarity in shapes of the upper and lower waveforms further indicates that for this subject and the electrode configuration employed the waveshape was not highly dependent on correct placement. A reliable, though weaker, waveform was obtained even when the electrodes were displaced somewhat from the position of the larynx. The EGG output could be taken as either of the outputs in FIG. 3C or, more preferably, the sum of the outputs. With other subjects, especially those producing a weak EGG signal, a dissimilarity of the waveforms of the upper and lower traces may occur even when the waveforms are similar in amplitude. This dissimilarity could be considered a warning that the traces must be interpreted with more caution. This additional self-checking ability is another advantage of a multielectrode EGG that did not exist in the prior art.

A multielectrode embodiment showing three pairs of electrodes is schematically illustrated in FIG. 4. In this embodiment the elements that are identical with those in the first embodiment are identified with the same reference characters. In addition to the first and second channels 30 and 32 described in regard to FIG. 2, and in addition to the first two pairs of electrodes 16,22 and 18,24, this embodiment employs a third channel 64 of substantially identical construction, which is also driven by the crystal oscillator 34 and has a parallel connection with a third pair of left and right electrodes 64 and 68. While this particular embodiment shows a three-channel parallel configuration, it should be apparent that it would not be difficult to add fourth, fifth, and further channels and corresponding electrodes, to provide a similar number of electroglottograph output signals The receiver circuits 80, 82, 84 are designed to efficiently demodulate an AM carrier in which the percent modulation is extremely small. As illustrated in FIG. 4, the AM detector 56 can be comprised of a pair of diodes 73,73 that connect to respective ends of a center-tapped secondary 72 of the transformer 52 to provide full-wave rectification. The values of the capacitor $C_a$ and the resistor $R_a$ are chosen to form a standard peak detecting demodulator, though the peak charging capacitor $C_a$ can be deleted, to form a rectified-average-value detector, with a slight decrease in output amplitude. A half-wave rectifier employing only one diode can also be used with a small decrease in efficiency. The amplifier 60 can be a suitably configured low-noise operational amplifier 74. The configuration shown provides a separate and lower gain for the dc output and a separate and much higher gain for the ac output, with the capacitor $C_b$ selected to separate ac and dc components for this purpose. By providing widely different gain values for the dc and ac components of the demodulator output, the amplifier 60 effectively separates the small ac variations from the large dc signal without the use of automatic level control systems that would vary the gain of the EGG. The equations determining the dc or low frequency gain, the ac gain and the value of $C_b$ required can be computed readily from the amplifier circuits, and are simplified when $R_{b1}$ is made equal to $R_{b2}$ and the ac gain is much larger than the dc gain. Both these conditions are preferable in this application. Under these conditions, the dc gain is substantially equal to $2R_{b1}/R_a$, the ac gain is equal to $R_c/R_a$ and the capacitor $C_b$ required can be computed from the inequality $$C_b >> \frac{R_c}{2\pi F_0 (R_{b1})^2}$$

where $F_0$ is the lowest repetition frequency expected for vocal fold vibration. When this inequality holds, the negative feedback current through $R_{b1}$ and $R_{b2}$ is eliminated for frequencies equal to or greater than $F_0$.

In the terminology of circuit theory, the amplifier 60 provides different gains for the dc and ac components by forming a transfer function for amplifier 60 which has a real zero at a radian frequency $\omega_z$ determined by $$\omega_z = 2/R_{b1}C_b$$

and a real pole at a radian frequency $\omega_p$ determined by $$\omega_p = R_c/R^2_{b1}C_b$$

Making $C_b$ approximately ten times greater than the right hand side of the aforementioned inequality will generally be enough to place $\omega_z$ and $\omega_p$ well below the desired frequency components in the EGG waveform, thus preserving its fidelity, while eliminating unwanted low frequency artifacts from the EGG signal. The precise value of $C_b$ could be made a parameter chosen by the user to match a specific application.

The capacitor $C_c$ further removes any RF ripple that remains after peak detection, and is chosen to make $R_c C_c$ smaller than the desired response time for the EGG signal (usually about ten to twenty microseconds). Additional external low-pass filtering of the ac output signals may be desirable to more thoroughly remove carrier ripple when the EGG signal is very weak.

The low pass filter formed by $R_d C_d$ and the high pass filter formed by $R_e C_e$ in the receiver circuit 80 both receive the amplified demodulated signal and separate the dc and the ac signals. For each RC pair, the values of R and C used should be chosen to satisfy the inequality $$R \cdot C >> \tfrac{1}{2}\pi F_0$$

where $F_0$ is again the lowest expected vocal fold vibration frequency. In a preferred embodiment, shown as FIG. 4a, $R_d$ is formed as a series connection of two resistances $R_{d1}$ and $R_{d2}$ which sum to $R_d$, and the values of $R_{d1}$, $R_{d2}$, and $C_d$ are chosen so as to form at the junction of $R_{d1}$ and $R_{d2}$ a transfer function which has a pole at the aforementioned value of $\omega_z$, and a zero at the aforementioned value of $\omega_p$. Thus, for the signal formed at the junction of $R_{d1}$ and $R_{d2}$, there will be canceling of the zero and the pole introduced by $C_d$, and the entire original demodulated signal will be reconstructed, with dc and ac components present in their original proportions. For this cancellation of the zero at $\omega_z$ and the pole at $\omega_p$ to occur, the values of $R_{d1}$, $R_{d2}$, and $C_d$ should be selected so as to satisfy the following two relations:

$$\frac{R_{d1}}{R_{d2}} = \frac{R_c}{2 R_{b1}}$$

and

-continued $$R_d C_d = R_{b1} C_b/2$$

Figure 5:
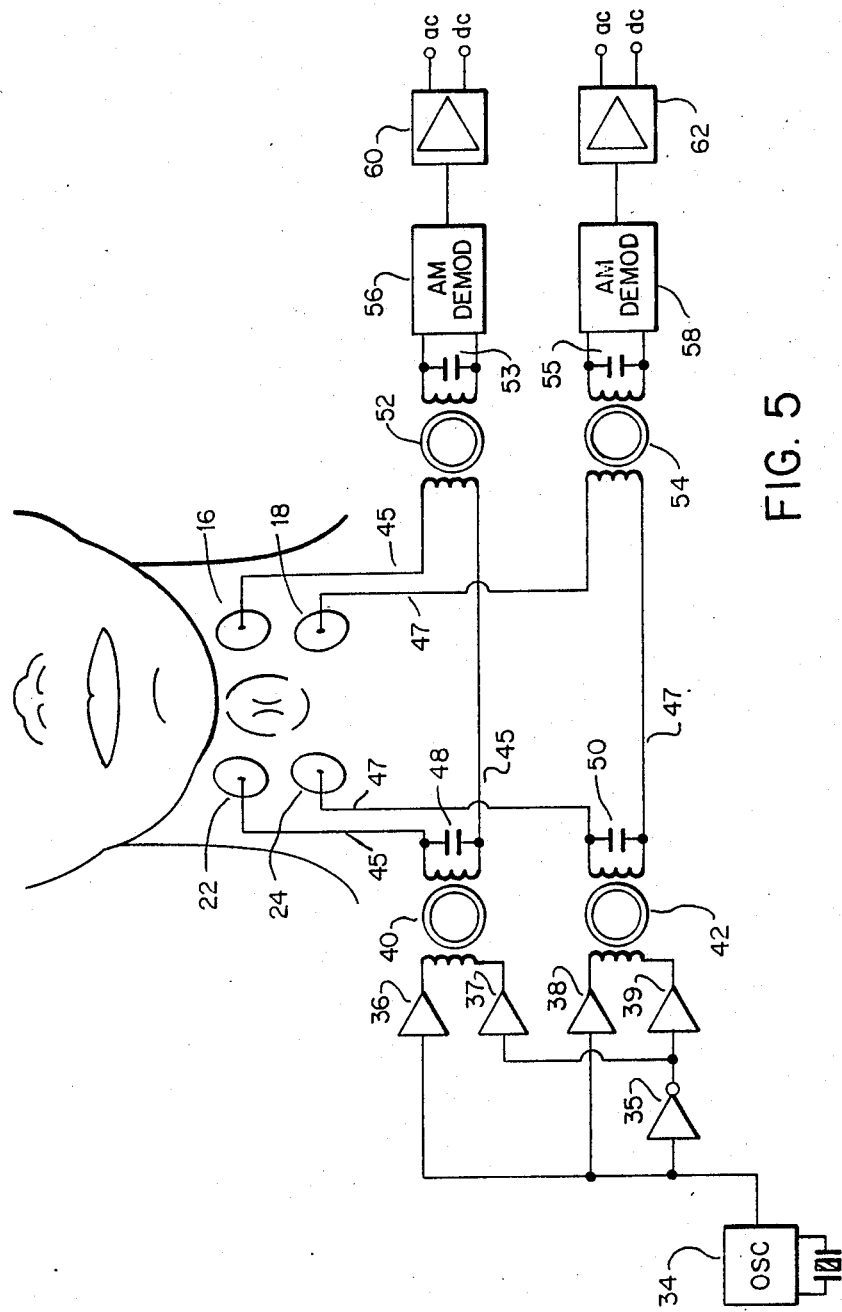
FIG. 5 is electrical schematic diagram of a series type EGG according to still another embodiment of this invention.

FIG. 5 illustrates an alternative series configuration, that is, an arrangement in which the secondary windings of the send transformers 40,42 and the primary windings of the receive transformers 52,54, are all connected in series across the impedance formed by the subject's neck, including the vocal folds. In this embodiment, the same elements that are also shown in the embodiment of FIG. 2 are identified with the same reference numbers. In this embodiment, the upper electrodes 16 and 22 are connected in series with the conducting path 45 and the send and receive transformers 40 and 52, while the lower electrodes 18,24 are connected in series with the conducting path 47 and the send and receive transformers 42 and 54.

This series configuration is a low impedance circuit, whereas the parallel configuration embodiment of FIG. 2 is a high impedance circuit. As the impedance across the subject's throat is on the order of 100 Ohms, the series configuration should optimally have send and receive circuit elements with impedances smaller than 100 Ohms, while those of the parallel configuration should have impedances greater than 100 Ohms.

Figure 6:
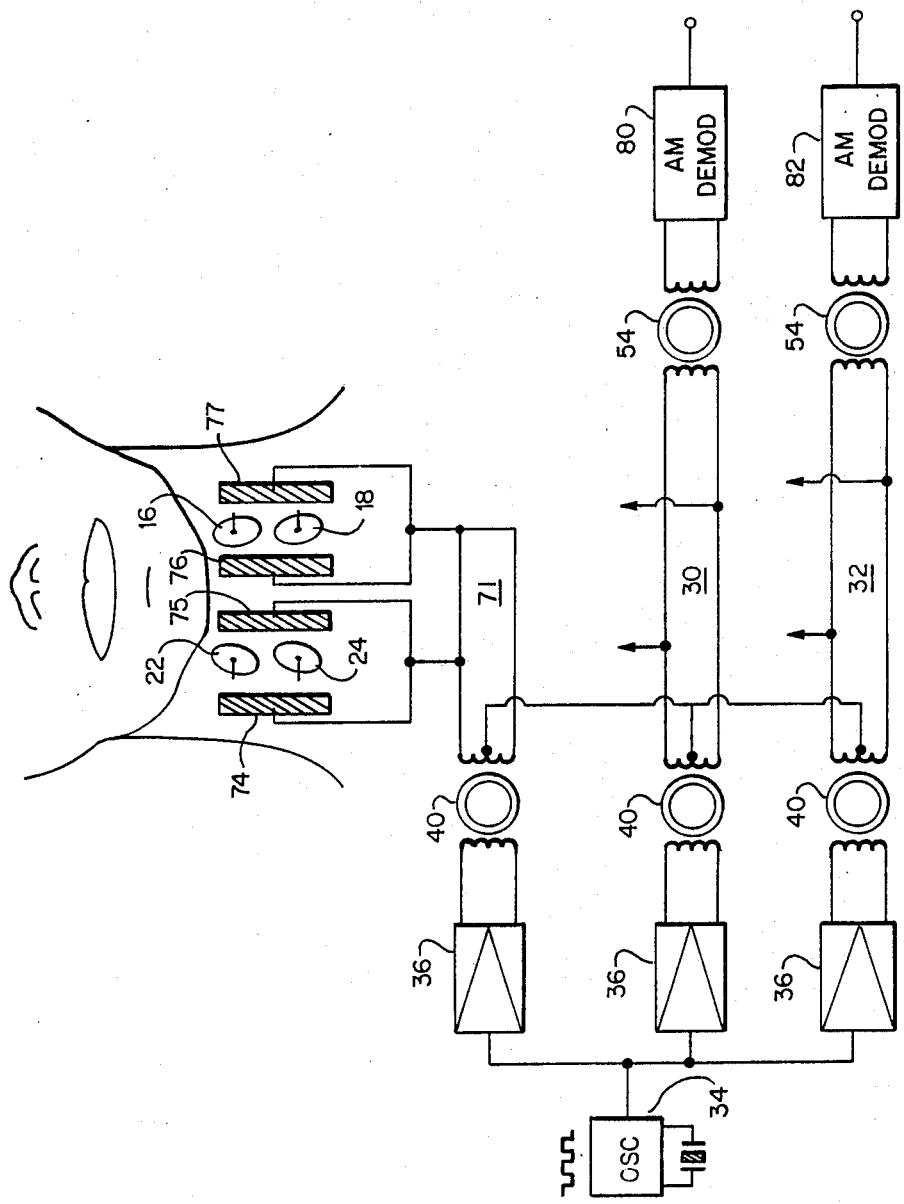
FIG. 6 is an electrical schematic diagram of a further embodiment of this invention which employs guard electrodes.
Figure 7:
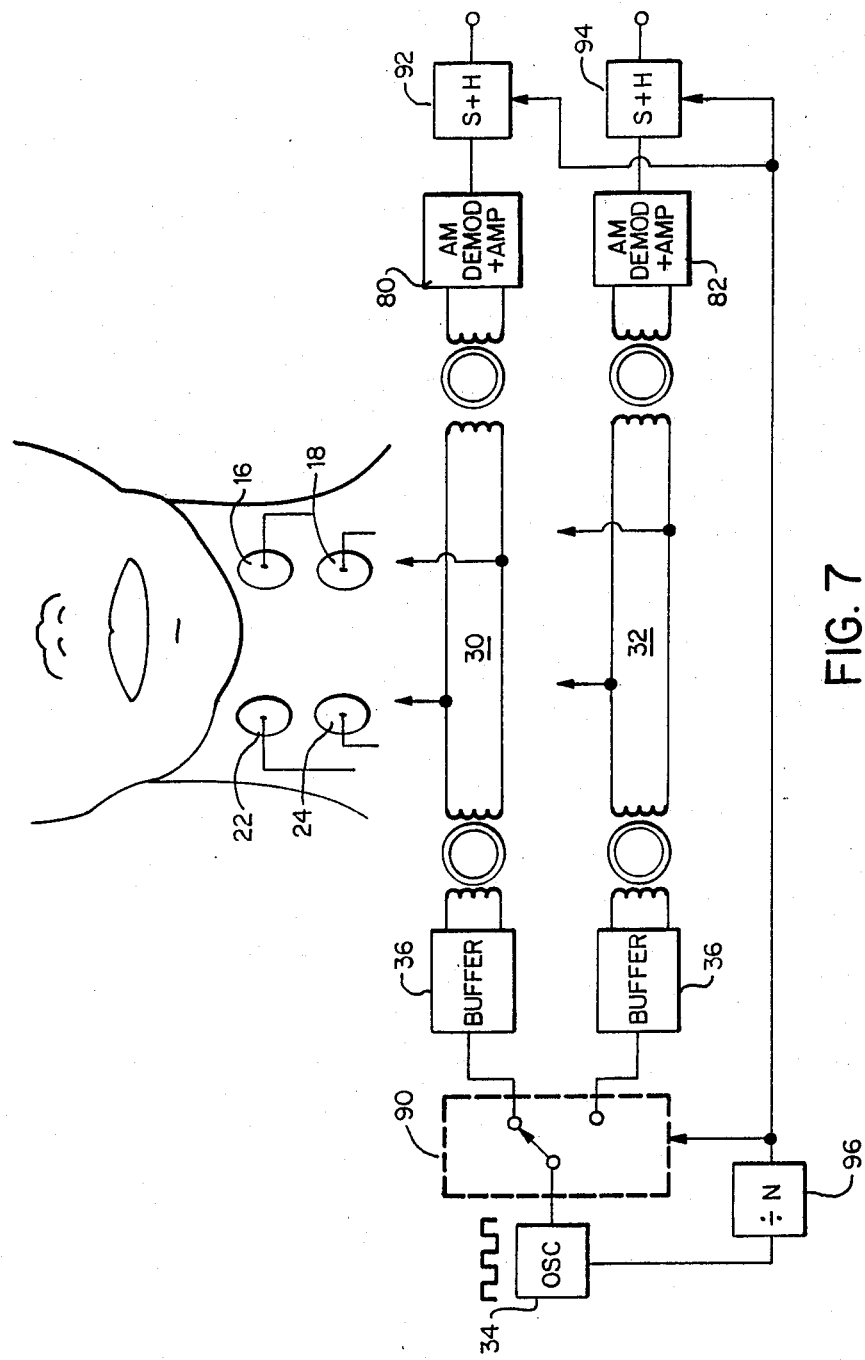
FIG. 7 is a schematic electrical diagram of an embodiment of this invention in which time-multiplexing of the various electrode pairs is employed.

Yet another embodiment of this invention is shown in FIG. 6, which is intended to increase the percent modulation of the RF carrier caused by the vocal fold contact. In the previous configurations, the electric fields that are produced by the various electrodes diverge within the neck along the horizontal plane to produce a fringing field. However, with the configuration shown in FIG. 3, the divergence of the electric fields along the horizontal plane can be reduced. In this embodiment, there is a guard channel 71 which provides a synchronized RF signal to pairs of elongated electrodes 74,75 and 76,77 disposed vertically along and on opposite sides of the electrodes 22,24 and 16,18 of each array 14,20. The secondaries of all send transformers are center-tapped in this embodiment, with all center taps connected together. This configures the electrodes so that the field between the two electrodes in each active electrode pair 22,16 and 24,18 does not diverge as much as without the guard electrodes. Thus, a greater proportion of the current between the active electrode pairs will be affected by vocal fold movements, provided that the electrode arrays are placed on the subject's neck so that the central portion of the field is aligned with the trachea-glottis-pharynx axis. The relative or percent change in the receive RF carrier caused by vocal fold contact will therefore be greater than with the electrical field of the previous embodiments. This, in turn, will reduce noise in the output that is added in the receiver and also any noise caused by the small instabilities in the amplitude and frequency of the RF carrier signal generated by the transmitter.

In each of the above embodiments, interchannel leakage of EGG signals is kept low by electrical isolation of the respective RF signals. However, some leakage or interaction will occur across the surface of the skin and within the neck tissues. This amount of interaction may not be objectionable and, with some electrode configurations, interaction of the electrical fields within the neck may actually increase the sensitivity of the system to small spatial differences. However, if it is desired to further reduce the interaction between channels, this can be accomplished by the embodiment shown in FIG.

7, which is a modification of the embodiment of FIG. 2 in which an electronic switch 90, which can be composed of standard logic circuits, provides an oscillator signal to only one channel at a time. The sample-and-hold circuits 92 and 94 in the receiver are synchronized with the switch 90, and output only the signal from the channel being energized. The switching and sampling frequency could be obtained by counting down from the oscillator frequency by the frequency-divider logic circuit 96. The switching frequency should be chosen high enough so as to sample each channel at a rate that is at least twice the highest signal frequency expected, in order to exceed the Nyquist rate for a band-limited signal, and could be between 25 KHz and 50 KHz for a two-channel system.

The battery operation in the above embodiments virtually eliminates power supply noise, in addition to providing an added safety factor to the subject. To minimize the noise introduced by the receiver electronics, the present embodiments have no receive-side RF amplifier, and the AM demodulator and post-demodulation signal amplifier are designed for minimum noise. However, in multi-channel arrays in which the size of the electrodes is rather small, a low noise RF amplifier can be introduced in advance of the demodulators. In such conditions, the send and receive transformers should be very carefully wound and designed to maximize the signal-to-noise ratio (SNR). The SNR can be measured on a calibrated simulated neck (not shown) comprised of a resistance of about 100 Ohms that is varied by some selectable small increment at a frequency that is within the range of the EGG apparatus.

Calibration of the tracking signal can also be performed readily. A preferred method is a reciprocal technique in which the electrode arrays are moved simultaneously by a small calibrated amount along their vertical axis, preferably a few millimeters and preferably in an oscillatory manner about the optimal vertical position for the speech or singing material for which the calibration is being performed. During this procedure, the subject preferably produces a continuous vocalization of a single speech sound typical of the material to be spoken or sung. The resulting variation in the tracking signal is recorded and used as a measure of the variation in the tracking signal to be expected when the arrays are held stationary on the neck and the larynx moves within the neck during the process of continuous speech or singing. During the calibration procedure, it is expected that the skin of the neck may move with the electrode arrays (instead of the electrodes moving over the skin), however, the occurrence of this should have no significant effect on the validity of the calibration.

With the electrode voltages and currents limited to accepted physiologically-safe vales, with the electrodes transformer-isolated from circuit power and ground potentials, and with the battery operation, the danger or discomfort from the electroglottograph of this invention i extremely small and is, to wit, negligible. On the other hand, there is a significant potential for aiding those at risk for or who have voice disorders, as well as for improving speech training procedures and singing pedagogy.

While the present invention has been described with reference to a few preferred embodiments, it should be understood that the invention is not limited to those precise embodiments; rather, many modifications and variations would present themselves to those of skill in the art without departing from the scope and spirit of this invention, as defined in the appended claims.

What is claimed is:

1. An electroglottograph for providing signals representing the variation with time of the area of contact between the vocal folds of a subject's larynx during speech, comprised of at least first and second channels; each said channel including signal source means which is isolated from the signal source means of the other channel and which produces a high frequency electrical carrier that is synchronized with the carrier from the signal source means in the other channel so as not to produce beats, respective right and left electrodes to be disposed in contact with the skin on the left and right sides of the subject's neck at the location of the larynx, detector means having an input coupled to the signal source means and the electrodes, the detector means providing a demodulated output signal having an ac component that indicated the variations of vocal fold contact area over time and a dc component, with the ac component of the demodulated signal consisting of components at and above the frequency at which the vocal fold movements tend to repeat, and the dc component of the demodulated output signal consisting of components substantially lower than the vocal repetition frequency.

2. An electroglottograph according to claim 1 wherein the right and left electrodes of the first channel are adapted to be disposed on the subject's neck posterior to respective left and right electrodes of the second channel so as to permit the detection of spatial differences along the vocal folds in the time patterning of the area of contact.

3. An electroglottograph according to claim 1 wherein said right and left electrodes of each channel are connected to respective send output leads and receive input leads in a parallel configuration.

4. An electroglottograph according to claim 1 wherein said right and left electrodes of each channel are connected to respective send output leads and receive input leads in a series configuration.

5. An electroglottograph according to claim 1 in which the signal source means of each channel includes an amplifier that includes a logic circuit having high and low levels and input terminals, with a common drive oscillator connected to the input terminals of the amplifying logic circuits of the first and second channels.

6. An electroglottograph according to claim 1 in which the amplifier which receives the demodulated output includes means to provide separate and different gains for ac and dc components, with the gain for the dc component being substantially smaller than the gain for the ac component, so that noise introduced by the amplifier is minimized.

7. An electroglottograph according to claim 6 in which the separate and different gains for ac and dc components are derived from a single operational amplifier circuit in which a branch from an output to a negative input thereof passes a substantially lower current to the negative input at EGG signal frequencies than it does at frequencies significantly lower than the range of EGG signal frequencies including dc.

8. An electroglottograph according to claim 1 wherein said electrodes are discs of between 0.5 and 1.5 square centimeters in effective area and are separated from one anther by a distance of substantially 5 to 10 mm.

9. An electroglottograph according to claim 1 in which a transformer is included in each channel to couple the electrodes of that channel to the signal source means or the detector means.

10. An electroglottograph according to claim 1 wherein said detector means each include an amplitude modulation detector of a type selected from either the peak-detecting type or rectified-average-value-type.

11. An electroglottograph according to claim 1 wherein said detector means each include a coherent detector.

12. An electroglottograph according to claim 1 further comprising a guard channel which includes at least one pair of elongated guard electrodes each extending alongside superposed electrodes of the first and second channels.

13. An electroglottograph according to claim 1 further comprising time multiplexing means in which the high frequency electrical carrier is applied to only certain channels at any one time by an electronic switch means and the outputs of only the selected channels are sampled by sampled-and-hold circuits that are synchronized with said electronic switch, whereby interaction between the channels is eliminated.

14. A process for identifying the position of a subject's larynx during voiced speech by use of a multielectrode electroglottograph of the type which has at least first and second channels, each said channel including signal source means which has oscillator means which is isolated from the signal source means of the other channel and which produces a high frequency carrier that is synchronized with the carrier in the other channel so as not to produce beats, respective left and right electrodes to be disposed in contact with the skin on the left and right sides of the subject's neck a the approximate location of the larynx, and respective demodulator means for detecting amplitude modulation of the carrier signal and providing a demodulated output signal that indicates variation of vocal fold contact area over time, said left and right electrodes each being connected to the output leads of the signal source means and the input leads of the demodulator means; the left and right electrodes of the first channel being disposed on the subject's neck vertically above the respective left and right electrodes of the second channel, so as to permit tracking of the vertical position of the larynx by variations in the relative amplitude of the ac components o the respective demodulated output signals; the method including producing a time-varying tracking signal based on the relative amplitudes of the respective demodulate output signals.

15. The process according to claim 14 wherein the step of providing said tracking signal includes producing a value representing the logarithm of the ratio of the respective channel output signal amplitudes.

16. The process according to claim 14 further comprising calibrating said tracking electroglottograph by a reciprocal process in which the right and left electrode arrays are simultaneously moved by a calibrated vertical distance during the production of a constant voiced speech sound, so that the resulting change in the tracking signal can be used as a measure of the sensitivity of the tracking signal to vertical movements of the larynx when the array position is held constant on the neck.

17. The process according to claim 14 further comprising adjusting the vertical position of the electrodes on the subject's neck until the relative amplitudes of the two channel output signals are substantially equal.

18. The process according to claim 14 further comprising automatically selecting as the electroglottograph output the output of the channel having the greatest output amplitude, or a suitably weighted summation of the outputs of neighboring channels having similarly strong output amplitudes.

19. The process according to claim 14 wherein said output signals for each channel each include an ac component and a dc component, further comprising combining the amplitudes of the ac and dc components of each channel in a ratio circuit to produce a signal that corresponds directly to the percentage modulation of the high frequency electrical carrier for the associated channel, and indirectly to percentage modulation of interelectrode neck impedance, as caused by the oscillatory variation of vocal fold contact area, thus providing an indication of signal reliability.

20. The process according to claim 19 wherein the amplitude of the ac component in each channel constitutes an approximate measure of percent modulation for that channel, with a fixed average value serving as the magnitude of the dc component.

21. The process according to claim 19 wherein the percent modulation of the various channels are electronically compared, and at every instant only the percent modulation of the channel having the greatest value of percent modulation is displayed.

* * * * *

UNITED STATES PATENT AND TRADEMARK OFFICE
CERTIFICATE OF CORRECTION

PATENT NO. : 4,909,261

DATED : March 20, 1990

INVENTOR(S) : Martin Rothenberg

It is certified that error appears in the above—identified patent and that said Letters Patent is hereby corrected as shown below:

In column 1, line 4, please insert:

--This invention was made with government support under Grant No. R01 NS-08919 awarded by the National Institutes of Health. The Government has certain rights in the invention.--

Signed and Sealed this

Fifteenth Day of December, 1992

Attest:

DOUGLAS B. COMER

*Attesting Officer*  *Acting Commissioner of Patents and Trademarks*